(12) United States Patent
Finley

(10) Patent No.: US 8,105,666 B2
(45) Date of Patent: Jan. 31, 2012

(54) COMPLIANT POLYMERIC COATINGS FOR INSERTABLE MEDICAL ARTICLES

(76) Inventor: Michael J. Finley, Saint Louis Park, MN (US)

(*) Notice: Subject to any disclaimer, the term of this patent is extended or adjusted under 35 U.S.C. 154(b) by 1382 days.

(21) Appl. No.: 11/376,671

(22) Filed: Mar. 14, 2006

(65) Prior Publication Data

US 2006/0210816 A1 Sep. 21, 2006

Related U.S. Application Data

(60) Provisional application No. 60/661,713, filed on Mar. 15, 2005.

(51) Int. Cl.
*B32B 1/08* (2006.01)
*B32B 27/08* (2006.01)
*B32B 27/32* (2006.01)
*B32B 15/02* (2006.01)
*F16L 11/04* (2006.01)
*A61F 2/06* (2006.01)
*A61F 2/02* (2006.01)
*A61F 2/82* (2006.01)
*A61M 31/00* (2006.01)
*A61M 29/00* (2006.01)

(52) U.S. Cl. ............ 428/34.1; 428/35.2; 428/35.3; 428/35.4; 428/35.7; 428/35.8; 428/36.6; 428/36.8; 428/36.91; 604/48; 604/93.01; 604/96.01; 623/1.1; 623/1.15; 623/1.49; 623/11.11

(58) Field of Classification Search .......... 428/34.1, 428/35.2, 35.3, 35.4, 35.7, 35.8, 35.9, 36.5, 428/36.6, 36.7, 36.8, 36.9, 36.91; 604/48, 604/93.01, 96.01; 623/1.1, 1.15, 1.49, 11.11
See application file for complete search history.

(56) References Cited

U.S. PATENT DOCUMENTS

| | | | |
|---|---|---|---|
| 5,002,582 A | 3/1991 | Guire et al. | |
| 5,414,075 A | 5/1995 | Swan et al. | |
| 5,563,056 A | 10/1996 | Swan et al. | |
| 5,660,848 A | 8/1997 | Moo-Young | |
| 5,714,360 A | 2/1998 | Swan et al. | |
| 5,731,087 A * | 3/1998 | Fan et al. | 428/412 |
| 5,782,908 A | 7/1998 | Cahalan et al. | |
| 5,800,412 A | 9/1998 | Zhang et al. | |

(Continued)

FOREIGN PATENT DOCUMENTS

WO  WO 03/055611  7/2003

OTHER PUBLICATIONS

International Search Report of International application No. PCT/US2006/009277, mailed Mar. 27, 2007 (6 pgs).

(Continued)

*Primary Examiner* — Walter B Aughenbaugh
(74) *Attorney, Agent, or Firm* — Kagan Binder, PLLC

(57) ABSTRACT

Compliant coatings for insertable medical articles are provided. In some aspects, the coating includes a diene polymer-containing layer, and a second coated layer that includes another polymer. The coating can be formed by coupling the polymer of the second coated layer to the first coated layer via latent reactive groups, such as photoreactive groups. In other aspects, the insertable medical article has a coating that provides different functional features to different surfaces of the article. The medical article can have a cylindrical shape with an interior surface having a first coating, and an exterior surface with a second coating, wherein the article also includes a plurality of openings.

24 Claims, 1 Drawing Sheet

U.S. PATENT DOCUMENTS

| | | |
|---|---|---|
| 5,858,653 A | 1/1999 | Duran et al. |
| 5,962,620 A * | 10/1999 | Reich et al. ............ 528/76 |
| 6,007,833 A | 12/1999 | Chudzik et al. |
| 6,278,018 B1 | 8/2001 | Swan |
| 6,524,268 B2 * | 2/2003 | Hayner et al. ............ 604/8 |
| 6,764,761 B2 | 7/2004 | Eu et al. |
| 6,890,348 B2 | 5/2005 | Sydney et al. |
| 7,311,980 B1 * | 12/2007 | Hossainy et al. ......... 428/480 |
| 2003/0215649 A1 | 11/2003 | Jelle |
| 2004/0030159 A1 | 2/2004 | Swan |
| 2004/0115412 A1 | 6/2004 | Baron et al. |
| 2004/0234703 A1 | 11/2004 | Frautschi |

OTHER PUBLICATIONS

Kennedy, et al., (2009) The synthesis and characterization of grafted random styrene butadiene for biomedical applications. J Mater Sci, 44: 889-896.

* cited by examiner

COMPLIANT POLYMERIC COATINGS FOR INSERTABLE MEDICAL ARTICLES

CROSS-REFERENCE TO RELATED APPLICATION

The present non-provisional Application claims the benefit of commonly owned provisional U.S. Patent Application having Ser. No. 60/661,713, filed on Mar. 15, 2005, and entitled COATING INCLUDING A DIENE POLYMER LAYER FOR MEDICAL ARTICLES.

FIELD OF THE INVENTION

The invention relates to polymeric coatings for insertable medical articles. One aspect of the invention relates to insertable medical articles having a compliant coated layer that includes a diene polymer. The diene polymer can be present in a coating that provides improved functionality to the article, such as improved lubricity. Another aspect of the invention relates to methods for providing a coating to a desired portion of an insertable medical article, and coated articles formed therefrom.

BACKGROUND OF THE INVENTION

Surface coatings can provide medical articles, such as those that are implanted or temporarily inserted into the body, with a variety of distinct benefits. These benefits include lubricity and wettability, passivity against protein absorption, antimicrobial properties, drug delivery, biocompatibility and hemocompatibility. The demand for medical articles having these types of coatings is rapidly increasing because they generally improve the function of the device upon implantation or insertion in the body. However, while these properties can provide clear advantages for the function of these devices, the preparation of these coatings can, in many cases, be technically challenging and also quite costly.

Medical articles are typically prepared from plastic or metal biomaterials, or combinations of these biomaterials. Generally, plastic medical articles provide good substrates for the bonding and immobilization of coating materials, as the plastic surface can be reacted with chemical groups that are provided with the coating material. On the other hand, the immobilization of coating materials on metal substrates is generally more challenging because, in many cases, the metal surface is not able to directly covalently bond the reactive group. To overcome this, a base layer of material, often called a "priming layer" or a "tie layer", is disposed on the surface to provide a material to which a subsequent coating material can react. Therefore, many metal-containing medical articles having coatings include two or more coated layers, at least one of which is a base layer that facilitates the immobilization of materials of a second layer.

To maintain the integrity of the coating, the material of the base layer should remain continuously contacted with the metal surface of the device after the coating is formed and during use of the coated device. Problems with the coating may be seen if a portion of the coated base layer separates from the surface, which can result in delamination of all or portions of the coated materials from the surface of the device. As a result, surface properties may be lost before or during use, for example, before or during implantation or insertion into the body.

For some medical articles which are flexed or bent during use, the material of the base layer should be compliant. A compliant base layer can prevent the coating from cracking or delaminating.

Parylene™ (poly(para-xylylene)) is commonly used as a base layer material. Parylene™ base layers are typically very thin (0.1 micron to 75 microns), continuous, inert, transparent, and conformal films. Parylene™ is applied to substrates in an evacuated deposition chamber by a process known as vapor deposition polymerization (VDP). This involves the spontaneous resublimation of a vapor that has been formed by heating di-para-xylylene, which is a white crystalline powder, at approximately 150° C., in a first reaction zone. The vapor resulting from this preliminary heating is then cleaved molecularly, or pyrolized, in a second zone at 650° C. to 700° C. to form para-xylylene, a very reactive monomer gas. This monomer gas is introduced to the deposition chamber, where it resublimates and polymerizes on substrates at room temperature and forms a transparent film. In the final stage, para-xylylene polymerizes spontaneously onto the surface of objects being coated. The coating grows as a conformal film (poly-para-xylylene) on all exposed substrate surfaces, edges and in crevices, at a predictable rate. Parylene™ formation is spontaneous, and no catalyst is necessary.

While the benefits of a Parylene™ base layer can be clearly seen, there are various drawbacks to using this process in coating processes for metal medical articles wherein a base or tie layer is needed to form a coating. For example, as indicated above, the process of Parylene™ deposition is rather involved and furthermore requires the use of costly apparatus to carry out the vapor deposition process. Also, in order to ensure that an adequate Parylene™ layer is formed on the surface of the device substrate, it is typically necessary to thoroughly remove oils and contaminants from the device surface. This can add time to the coating process and also subjects the coated article to potential defects in the coating if it not cleaned adequately. Furthermore, in order to promote sufficient adhesion between the device surface and Parylene™ layer, the surface of the metal article typically needs to be pretreated with a silane material. This, again, can add time and expense to the coating process.

Another approach is to apply fluorinated materials such as Teflon to the metal surface. These coatings, however, can be excessively thick, have relatively low adhesion and elasticity, and can crack under stress.

Improved coating processes are therefore needed that improve the efficiency and costs that are associated with coating medical articles.

SUMMARY OF THE INVENTION

The present invention is related to improved coatings for insertable medical articles that can be changed in size, shape, or configuration during a medical process. The coatings of the present invention are very compliant and can be formed on medical articles that are inserted into a subject during a medical procedure. The insertable articles can be flexed or expanded during a medical procedure that introduces the article temporarily or permanently into the body. Wires, balloons, distal protection devices, stents, and coils exemplify these insertable medical articles. Insertable medical articles having the inventive coatings as described herein can be extensively manipulated following insertion without risking cracking or delamination of the coatings.

The coatings of the invention provide improved functionality to the article. For example, in some aspects, the coating provides a lubricious surface on one or more portions of the article. The lubricious surface can facilitate movement of the article within the body in a process wherein the article is also subject to flexion or expansion. The functionality of the medical article may be enhanced by other properties of the coating.

For example, in some aspects the coating may be capable of releasing of a therapeutic substance.

In one aspect of the invention, the coating includes a first coated layer that includes a diene polymer. The diene polymer is not covalently bonded to the surface of the article. The coating also includes a second coated layer that includes a hydrophilic polymer, which can provide a lubricious surface and facilitate movement of the coated article within the body. The diene polymer does not stiffen the article, and allows for continued expansion and flexion of the article, as well as improved movement of the article, during a medical procedure. These coatings demonstrate excellent lubricity, even after having been placed under physical challenge. It is thought this improved lubricity is due at least in part to very good adhesion between the polymeric material of the first coated layer and the surface of the article. In some cases the surface of the article includes a metal surface.

The diene polymer can be a butadiene polymer, such as poly(1,2 butadiene). According to the invention, poly(1,2 butadiene) has been determined to be an excellent coating material for flexible or expandable medical articles. The diene polymer can have a Tg in the range of −40° C. to 0° C., and more preferably in the range of −15° C. to 0° C.

The diene polymer-containing first coated layer can also include other optional components, such as additional polymeric components. These components can be blended with the diene polymer. For example, bioactive agents can included and released from the first coated layer.

In some aspects the second coated layer is in contact with the first coated layer. In some aspects the coating also includes a latent reactive group that has been activated to covalently bond components of the coating together. In one preferred aspect, the butadiene polymer of the first coated layer is covalently bonded to the hydrophilic polymer. Preferably the diene polymer is bonded to the first coated layer via photoreactive groups.

The present invention provides a number of advantages for preparing coatings on the surface of flexible or expandable medical articles, and also for the use of these coated articles in medical processes. One distinct benefit of the present invention is the ability to form a multi-layer coating in a very cost effective and efficient manner. Coating compositions for forming the first coated layer that include a diene polymer, such as a butadiene polymer, are inexpensive and are readily prepared. These compositions can be coated on the surface of medical articles with great ease, for example, by dip-coating or by brush-coating. The coating methods do not require the use of expensive equipment, such as plasma deposition apparatus, for formation of the coating.

The method for forming a coating on an insertable medical article includes the steps of (a) disposing a composition comprising a diene polymer to form a first coated layer, and (b) disposing a composition comprising a hydrophilic polymer on the first coated layer to form a second coated layer.

In some aspects of the invention a latent reactive group is included in a step in the coating method. The latent reactive group can be activated in a step in the coating method to form covalent bonds between one or more components of the coating. The diene polymer, immobilized in the first coated layer, provides an excellent target for activated latent reactive groups. In some aspects the latent reactive groups can be used to bond the hydrophilic polymer of a second coated layer to the diene polymer, allowing formation of a coating with excellent durability.

Latent reactive groups can be pendent from the hydrophilic polymer, independent of the hydrophilic polymer, or both. In preferred aspects, the latent reactive groups are pendent from the hydrophilic polymer. In preferred aspects, the latent reactive groups are photoreactive groups.

In another aspect, the invention provides insertable medical articles having coatings that provide different functional features to different surfaces of the article. In some aspects, one portion of the medical article includes a coated layer that provides lubricity to the surface while another portion of the article can have a coating that provides a different functional property.

For instance, a lubricious coating can be formed on an outer surface of the article that is in contact with a tissue. The lubricious coating can facilitate movement of the surface over the tissue. The article has an inner surface having a coating that is different than the coating of the outer surface. For example, the coating of the inner surface can be different in terms of lubricity. This can be important in some aspects of the invention, for example, where the inner surface of the coated article is in contact with another article and frictional forces are desired between the two articles. These coatings can be formed in a very efficient and cost-effective manner.

As indicated, the inventive methods and compositions are particularly useful for forming coatings on the surface of articles that undergo flexion or expansion during use, such as coils and wires. However, many of these types of insertable medical articles also have openings in a surface of the article (such as gaps, pores, fenestrations, apertures, etc.). These openings can complicate a coating process involving forming coatings on different surfaces of the article.

In the course of providing the inventive coatings to a medical article, it was advantageously discovered that an efficient and effective coating process could be performed on an insertable medical article having openings, to provide an article having different coated surfaces. In this aspect, the medical article comprises a cylindrical shape with an exterior surface, an interior surface, a first end, a second end, and a plurality of openings between the first and second ends. The coating method includes the steps of (a) disposing a composition comprising a first polymer to form a first coated layer on the exterior and interior surfaces of the article, wherein the first coated layer substantially bridges the openings in the article, and (b) disposing a composition comprising a second polymer to form a second coated layer on the exterior surface of the article.

In forming the first coated layer, the openings in the article are blocked to the extent that they prevent a subsequently applied coating material (e.g., the second coating composition including the hydrophilic polymer) from entering the openings. Subsequently, the second coating composition is disposed on the article. The second composition is blocked from being disposed on the inner surface due to the first coated layer. A second coated layer is formed on the outer surface of the article, but not the inner surface of the article.

In some cases, step (a) involves disposing a composition comprising a diene polymer, such as a butadiene polymer, to form a first coated layer on the exterior and interior surfaces of the article. In some cases, the method includes a step of coupling the second polymer of the second coated layer to the first polymer of the first coated layer. The second polymer can include a hydrophilic polymer bonded to the first polymer via latent reactive groups.

In some aspects, the plurality of openings comprises an opening having a width of 76 μm or less.

The method can be used to form coating on the exterior of the article that is lubricious. An exemplary article is a wire formed into a helical shape, for example, a coil. In this article gaps between the coiled wire represent the openings between the first and second ends. The method can be used to provide such a coating to medical articles selected from the group consisting of guidewires and catheter coils.

BRIEF DESCRIPTION OF THE DRAWINGS

FIG. 1(a) is a schematic representation of an insertable medical article having a coiled structure.

FIG. 1(*c*) is a cross sectional view of the coiled structure having a first coating.

FIG. 1(*d*) is a cross sectional view of the coiled structure having a first and second coating.

DETAILED DESCRIPTION

Figure 1:
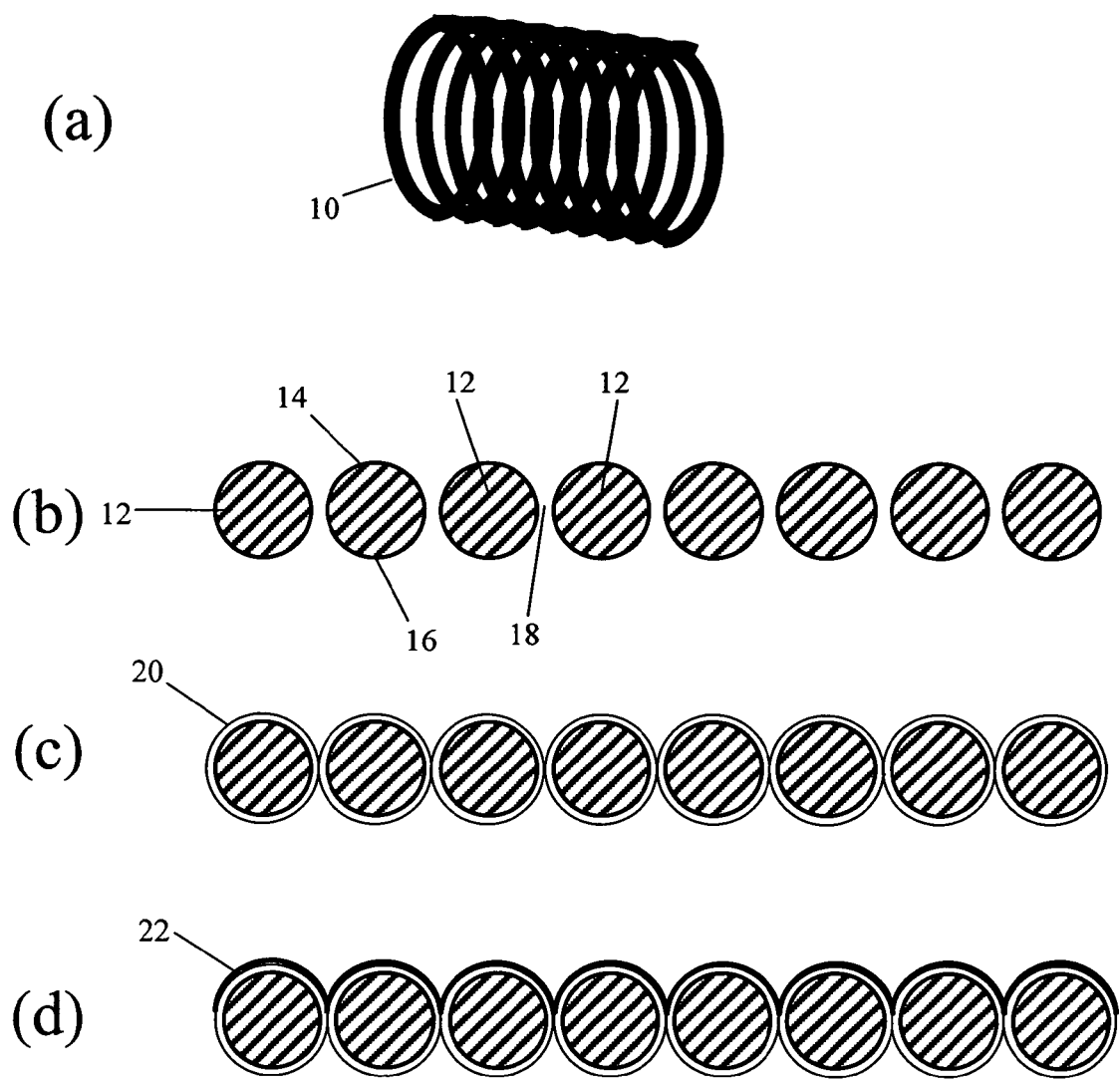
FIG. 1(*b*) is a cross sectional view of the coiled structure.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As used herein, the term "layer" or "coated layer" will refer to a layer of one or more coated materials of sufficient dimensions (for example, thickness and area) for its intended use over the entire, or less than the entire, portion of a medical article surface. A "coating" as described herein can include one or more "coated layers," each coated layer including one or more coating components.

If more than one coated layer is applied to the surface of an article, it is typically applied successively. For example, a coating is typically formed by dipping, spraying, or brushing the coating solution on an article to form a layer, and then drying the coated layer. In some preferred embodiments, the coating composition is applied by dip-coating. The process can be repeated to provide a coating having multiple coated layers.

For example, one aspect of the invention is directed to methods for preparing a coating on a surface of a medical article, the coatings including a first coated layer that includes a diene polymer. In a preferred aspect, a coated layer of the inventive coatings includes a butadiene polymer, also referred to herein as a poly(butadiene).

Other coated layers can present in the coating and these can be the same as or different than the diene polymer-containing layer. The suitability of the coating composition for use with a particular medical article, and in turn, the suitability of the application technique, can be evaluated by those skilled in the art, given the present description.

A "diene polymer" refers to homopolymers and copolymers that include diene monomeric units, including linear and branched homopolymers and copolymers. Exemplary diene polymers include those that have butadiene and/or isoprene monomeric units.

A butadiene polymer can include one or more butadiene monomeric units which can be selected from the monomeric unit structures (a), (b), or (c):

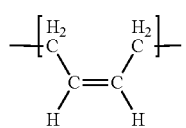

(a)

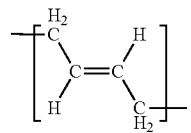

(b)

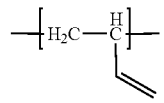

(c)

Contemplated butadiene polymers include poly(cis 1,4 butadiene), poly(trans 1,4 butadiene), and, preferably poly(1,2 butadiene), and isotactic, atactic, and syndiotactic polymers thereof. For example, a preferred diene polymer includes predominantly 1,2 butadiene monomeric units. According to the invention, it has been found that 1,2 butadiene-containing polymers can form coatings with excellent durability.

An isoprene polymer can include one or more isoprene monomeric units which can be selected from the monomeric unit structures (d), (e), or (f):

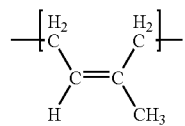

(d)

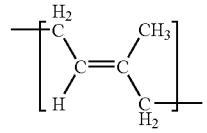

(e)

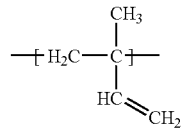

(f)

Contemplated isoprene polymers include poly(cis 1,4 isoprene), poly(trans 1,4 isoprene), and preferably poly(1,2 isoprene), and isotactic, atactic, and syndiotactic polymers thereof.

In some aspects of the invention, a diene homopolymer is used as a component to form the first coated layer wherein the monomeric units of the homopolymer are selected from any one of the monomeric units (a) through (f). In a preferred aspect, a diene homopolymer consisting of one of the monomeric units (c) or (f) is used as a component to form the first coated layer. A 1,2 butadiene homopolymer is most preferred.

The diene polymer present in the first coated layer can also be a copolymer. The term "copolymer" is used in its broadest sense and includes any sort of copolymer configuration wherein two different monomeric units are present. The diene copolymer can be formed by polymerizing diene monomeric units with one or more compatible comonomers. Suitable comonomers include, but are not limited to, other diene monomers and vinyl monomers, and monomers that include aliphatic or non-polar groups. In some aspects, preferred butadiene polymers include homopolymers and copolymers that provide coatings that allow the coated article to maintain good flexibility.

Diene copolymers include linear copolymers, branched copolymers, graft copolymers, including dendrimers, and star forms of copolymers. A diene copolymer can include any diene monomeric unit, such as butadiene or isoprene monomeric units. One example of a diene copolymer is poly(1,2 butadiene-co-1,2 isoprene). The diene copolymer can also include butadiene or isoprene monomeric units in combination with other monomeric units that are not butadiene or isoprene monomeric units.

As used herein, a butadiene copolymer contains predominantly butadiene monomeric units, that is, greater than 50% of the monomeric units are butadiene monomeric units. For example, a preferred butadiene copolymer includes predominantly 1,2 butadiene monomeric units. A butadiene copolymer can contain greater than 50%, 60%, 70%, 80%, 90%, or 95% 1,2 butadiene monomeric units.

Other suitable comonomers that can be included in a diene copolymer include, but are not limited to, vinyl monomers, and monomers that include aliphatic or non-polar groups. In some embodiments the comonomer is a non-aromatic compound. Examples of suitable non-aromatic comonomers include acrylonitrile, acrylate monomers such as methyl acrylate, and acetate monomers such as vinyl acetate. Examples of specific non-aromatic butadiene copolymers include poly(butadiene-co-acrylonitrile), polybutadiene-block-polyisoprene, polybutadiene-graft-poly(methyl acrylate-co-acrylonitrile). In some embodiments the diene polymer is a non-aromatic butadiene copolymer.

In other aspects, aromatic comonomers can be used in a diene copolymer. If a diene polymer including aromatic comonomers is used it preferably provides a coating which does not limit the flexibility of the article. For example, it can be acceptable to use diene copolymers having aromatic monomer units which provide a coating composition wherein the Tg of the coating composition is in the range of −40° C. to about 0° C. Aromatic comonomers include styrene monomers such as styrene, p-methylstyrene, o-methylstyrene, and α-methylstyrene. Examples of specific aromatic butadiene copolymers include poly(styrene-co-butadiene), polybutadiene-block-polystyrene, poly(styrene-co-butadiene-co-acrylonitrile), and poly(styrene-co-butadiene-co-methyl methacrylate).

Suitable diene polymers generally have a molecular weight of greater than 3,000 Da, and preferred diene polymers have a molecular weight in the range of about $1\times10^4$ Da to about $2\times10^5$ Da.

Prior to providing a first coated layer, the diene polymer that is used to form the first coated layer is preferably predominantly unsaturated. While it is recognized that the diene polymer or copolymer includes carbon-carbon bond unsaturation, wherein the double bond can be utilized in both crosslinking and derivation reactions, it preferred that the diene polymer is disposed on the surface of the article in a predominantly unsaturated form. The degree of unsaturation of the diene polymer is preferably in the range of 50% to 99% and more preferably in the range of 85% to 95%. In some aspects, the presence of unsaturated groups facilitates the bonding of the hydrophilic polymer of the second coated layer to the diene polymer. The presence of unsaturated groups can improve the durability of the coating by allowing for crosslinking between diene polymers of the first coated layer. Such crosslinking can be promoted by applying a source of activating energy, which can be provided in embodiments wherein a photoreactive group is used for form the coating, for example, the coupling of the hydrophilic polymer to the first coated layer.

The polymer composition of the first coated layer, which includes the diene polymer, generally has a glass transition temperature ($T_g$) in a range that allows a compliant coating to be formed on the surface of the article. In many aspects of the invention, the diene polymer is the predominant polymer in the first coated layer, and it is preferred that the diene polymer has a glass transition temperature ($T_g$) in range of about −40° C. to about 0° C., and more preferably in the range of about −15° C. to about 0° C. For example, poly(1,2 butadiene) homopolymer has a $T_g$ of about −9° C. In embodiments wherein the diene polymer is a copolymer, or the diene polymer present in a polymer blend, a single $T_g$ may be observed, which may lie between the $T_g$ of the corresponding pure homopolymers. In the case wherein the composition of the first coated layer includes a diene copolymer, or a blend of polymers which includes diene polymer, the composition can be prepared to have a $T_g$ in this target range, that is, between about −40° C. to about 0° C., and more preferably in the range of about −15° C. to about −0° C. For example, a poly(1,2 butadiene) copolymer can be prepared to have a $T_g$ in this range, or a poly(1,2 butadiene) polymer can be blended with one or more compatible polymers to provide a polymer blend having a $T_g$ in this range. $T_g$ can be measured by any suitable technique, e.g., dilatometry, refractive index, differential scanning calorimetry, dynamic mechanical measurement, and dielectric measurement.

In some aspects, the diene polymer includes a butadiene polymer. The butadiene polymer can be of any suitable form, as described herein, including forms such as a poly(butadiene)-block copolymer or a poly(butadiene)-graft copolymer. Suitable butadiene polymers, such as poly(1,2 butadiene), can be commercially obtained from any one of a number of sources, including, for example, Scientific Polymer Products (Ontario, N.Y.).

The synthesis of butadiene polymers is well known in the art. The synthesis of butadiene polymers has been described in various texts (see, for example, *Principles of Polymerization*, $2^{nd}$ Edition, Odian G., John Wiley and Sons, (1981). Synthesis of butadiene can be carried out using a transition metal (e.g., Nd, Ni, or Co) complex or an alkyl metal like butyllithium, as a catalyst. The polymerization reaction is very exothermic and typically is carried out in the presence of a solvent(s) such as hexane, cyclohexane, benzene, or toluene, to control the rate of reaction and reduce the viscosity of the polymer solution. Polymerization can be carried out, for example, using 80:20 solvent to monomer ratios. Batch or continuous processes can be carried out for polymerization. A particular polymerization process can be carried out to provide a butadiene polymer having a desired monomer content.

For example, anionic catalysis (e.g., alkyllithium) produces a polybutadiene polymer with about 40% cis, 50% trans, and 10% vinyl (1,2 butadiene) monomeric units. The percentage vinyl monomeric units can be increased in this type of polymerization by using polar modifiers. Suitable polar modifiers include nitrogen- or oxygen-containing compounds.

Transition metal (Ziegler) catalysis can be carried out to produce poly(butadiene) having a high content of monomeric units with the cis-1,4 configuration. Poly(butadiene) with a high cis monomer content also shows lower $T_g$ as compared to poly(butadiene) prepared form alkyllithium-based catalysis, due to the presence of pendent vinyl groups on the poly(1,2 butadiene).

Neodymium catalysis produces poly(butadiene) with a very high cis content (~99%) and provides for a relatively high proportion of linear poly(butadiene) (non-branched). Cobalt catalysis produces highly branched poly(butadiene)

with low solution viscosity. Nickel catalysis produces poly (butadiene) with an intermediate level of branching.

These, or other types of polymerization processes that are known in the art, can be carried to prepare a butadiene homopolymer or copolymer.

Other types of reactions can be performed to prepare diene copolymers, such as butadiene block copolymers. Diene polymers that have terminal functional group(s), for example, hydroxyl terminated poly(butadiene), can be used in the coating composition or can be used to prepare a copolymer which can be used as a component in the first coated layer. Diene polymers that have terminal functional groups can be used in derivation reactions to add structure to the ends of these polymers. For example, hydroxyl terminated butadiene can be chain extended with di- and polyisocyanates to produce diene copolymers having urethane linkages, or reacted with carboxylic acids, acid chlorides, or anhydrides to produce diene copolymers having urethane linkages. Butadiene polymers having terminal reactive groups can be commercially obtained from, for example, Sartomer (Exton, Pa.).

The first coated layer including the diene polymer can also include other components, such as additional polymeric components that can be blended with the diene polymer. Any additional polymeric components that are compatibly blended or dispersed with the diene polymer can be used.

In some embodiments of the invention, the first coated layer can be formed from blends of polymers, the blend including a diene polymer and one or more other different suitable compatible polymers. A suitable compatible polymer is that which can be blended in the same or similar solvent as the diene polymer. In some embodiments, the blend can include a compatible polymer that is similar to the diene polymer, such as blends of two different diene polymers. The blend can be prepared to have a $T_g$ in the ranges as described herein.

One example of a diene polymer blend is a butadiene homopolymer and a butadiene copolymer, such as poly(butadiene-co-isoprene) polymer. Another example of a blend is a butadiene homopolymer with an isoprene homopolymer. Yet another example of a blend is two different butadiene copolymers. Another specific blend includes poly(1,2 butadiene) and another polymer.

In other embodiments, suitable blends can include a diene polymer and another polymer that is different than the diene polymer, such as polymers that do not include any diene monomers. Exemplary polymers (including both copolymers and homopolymers) that can be blended with the diene polymer include poly(ethylene-co-vinyl acetate); poly(ethylene-co-alkyl acrylates), such as poly(ethylene-co-methyl acrylate), poly(ethylene-co-ethyl acrylate) and poly(ethylene-co-butyl acrylate); poly(ethylene-co-propylene); ethylene copolymers with other alkylenes, such as poly(ethylene-co-1-butene), poly(ethylene-co-1-butene-co-1-hexene), poly(ethylene-co-1-octene) and poly(ethylene-co-propylene-co-5-methylene-2-norborene); poly(1-butene), poly(2-butene), polyisobutylene and copolymers of the butene monomers; and epichlorohydrin-containing polymers, such as polyepichlorohydrin and poly(epichlorohydrin-co-ethylene oxide). Polymers that can be blended with the poly(butadiene) polymer can be obtained from various commercial sources, including Sigma-Aldrich (see 2003-2004 Aldrich Handbook of Fine Chemicals and Laboratory Equipment), or can be prepared according to polymerization techniques commonly used in the art. The blend of polymers can be chosen to provide a composition having a $T_g$ in the ranges as described herein.

In exemplary aspects of the invention, the diene polymer is the predominant component of the coating composition used to form the diene polymer coated layer. In these aspects, some components in small amounts may be present, such as components that affect the stability of the composition. It is also recognized that other components may be present in the composition but that are generally not intentionally added, such as impurities.

As indicated, the first coating composition includes, in the least, a diene polymer in a suitable solvent system. One or more other optional materials, such as other polymers, can be present in the first coating composition. Other, optional additional components, which can be non-polymeric, can be present in the first coating composition, such as those that improve the formation of the first coating layer. These optional additional components can include, for example, photoreactive groups that can promote crosslinking of the polymers present in the first coated layer. Suitable photoreactive groups include moieties such as benzophenone, benzoyl benzoic acid (BBA), and the like.

Bioactive agents can also be included and released from the first coated layer. Exemplary bioactive agents include, but are not limited to, antibiotics, anti-inflammatory agents, antiproliferative agents, immunomodulatory agents, anti-mitotics and anesthetics. Particularly useful bioactive agents of these classes include macrolide antibiotics such as rapamycin (triene macrolide antibiotic) and rapamycin analogs; immunomodulatory agents such as ABT-578; anti-mitotics including taxoid drugs such as paclitaxel and docetaxel; anti-inflammatory agents such as dexamethasone and betamethasone; and anesthetics such as lidocaine or tetracaine.

A coating composition can be prepared that includes a diene polymer, such as poly(butadiene), in an amount sufficient for the formation of a first coated layer on the surface of the article. The first coating composition preferably has a viscosity that is suitable for the type of coating process performed. In order to prepare a coating composition, the diene polymer and any other optional component, can be dissolved or suspended in a suitable solvent or mixture of solvents. In preferred aspects, the viscosity of the coating composition is in the range of 5 to 200 cP (at about 25° C.). In preferred aspects the diene polymer is dissolved or suspended at a concentration in the range of about 3% to about 7% weight/volume (w/v). In some aspects, if more than one polymer is present in the first coating composition, the combined amount of polymeric materials can be in this range.

Preferred solvents for the first coating composition include aromatic compounds such as toluene and xylene, and ethers such as tetrahydrofuran. Other suitable solvents include halogenated alkanes such as methylene chloride and chloroform; and amides such as dimethylformamide (DMF). Combinations of one or more of these or other solvents can also be used. The type of solvent system used can be chosen according to the diene polymer, and any other optional component present in the first coating composition.

The coating process can be carried out at a temperature suitable to provide a coating to the surface, or a portion of the surface, of the article. Preferably, the coating process is carried out at a temperature in the range of 10° C. to 50° C., and more preferably at a temperature in the range of 15° C. to 25° C. However, the actual coating temperature can be chosen based on aspects of the first coating composition, including the solvent system and the polymeric component(s), and also the method used to dispose the first coating composition on the surface of the article. For example, if the first coating composition has a relatively high viscosity, and/or the solvent system has a high boiling point it may be desirable to apply the coating at a temperature that is at the upper end of the temperature range. Conversely, if the first coating composition has a relatively low viscosity, and/or the solvent system has a low boiling point it may be desirable to apply the coating at a temperature that is at the lower end of the temperature range.

Prior to disposing the first coating composition on the surface of the article, the article can be cleaned using any suitable technique. As described herein, one distinct advantage of the invention is that the cleaning of the surface is not required to be as rigorous as compared to other coating processes, such as those involving plasma deposition. For example, cleaning processes that include treating the surface using an alcohol such as isopropyl alcohol and then using a commercially available cleaning solution to further cleanse the surface are not required but can be optionally performed in some cases. Cleaning steps such as rinsing the article in distilled water or a different liquid, such as an alcohol, may be sufficient to clean the article according to the invention. Agitation or other mechanical action, such as sonication, may also be used in these cleaning processes. It is understood that while extensive cleaning processes are not required to be performed prior to forming a first coated layer, they nonetheless may be performed, if desired.

Also, another distinct advantage of the invention is the article surface does not require functionalization prior to forming the first coated layer. For example, it is not required to pre-treat the metal surface with an oxidizing agent to functionalize the surface of the article, wherein the functionalization is intended to create reactive species, such as reactive metal oxides, on the surface of the article. By not requiring a functionalization step the coating process can be improved in terms of cost and time that would otherwise be added during one or more steps that lead to functionalization of the article surface.

Any suitable coating process can be carried out to dispose the first coating composition on the surface, or a portion of the surface, of the article or article to form a coated layer. A preferred method for applying the coating composition is a straightforward method such as dip-coating. A typical dip-coating procedure involves immersing the article to be coated in the first coating composition, dwelling the object in the composition for a period of time (a standard time is generally less than about 30 seconds, and can even be less that 10 seconds in many cases), and then removing the article from the composition. After the article has been dip-coated in the coating solution, it is removed and dried. Drying can be carried out using any suitable method, including air-drying the dip coated article. Times up to 30 minutes can be sufficient to dry the coated article although shorter times may be also sufficient.

Other straightforward methods such as brushing, swabbing, or painting the first coating composition on the surface of the article can be performed to provide the first coated layer. Alternatively, the first coating composition can be spray coated onto the surface of the article. If spray coating is performed it is preferable to utilize a spray coating technique suitable for solutions having a higher viscosity.

Optionally, after the composition that includes the diene polymer is disposed on the surface, the coated layer can be treated to promote crosslinking of the polymeric material in the first coated layer. Crosslinking can be promoted by treating the coated article with UV radiation, which can be performed before and/or after the first coated layer dries.

The first coating composition including the diene polymer is particularly suitable for providing a base coat to articles that undergo a change in size, shape, or configuration, during a medical procedure. For example, the article may expand, swell, inflate, enlarge, stretch, contract, deflate, collapse, shrink, flex, bend, twist, curve, or combinations thereof. For example, an insertable medical article that is capable of "expansion" can increase and/or decrease in size or volume, or can increase and/or decrease in one or more dimensions. An insertable medical article that is capable of "flexion" can bend at one or more points during a medical procedure.

Advantageously, the medical article can be subject to a change in size, shape, or configuration by one or more manipulations performed during a medical procedure, and retain the beneficial surface properties as provided by the diene polymer containing coating. During or after the medical procedure, the functionality of the medical article may be further enhanced by other properties of the coating, such as delivery of a therapeutic substance from the poly(butadiene) layer-containing coating.

The first coating composition including the diene polymer is particularly suitable for providing a base coat to articles that include a metal surface. However, the composition can be suitably applied on any sort of biomaterial to form a first coated layer. Although many articles are constructed from substantially all metal materials, such as alloys, some may be constructed from both non-metal and metal materials, where at least a portion of the surface of the article is metal. The metal surface may be a thin surface layer. Such surfaces can be formed by any method including sputter coating metal onto all or portions of the surface of the article.

Metals that can be used in medical articles include platinum, gold, or tungsten, as well as other metals such as rhenium, palladium, rhodium, ruthenium, titanium, nickel, and alloys of these metals, such as stainless steel, titanium/nickel, nitinol alloys, and platinum/iridium alloys. These metals, including other alloys or combinations, can be suitable substrates for disposing the first coating composition on.

Other surfaces that can be optionally coated include those that include human tissue such as bone, cartilage, skin and teeth; or other organic materials such as wood, cellulose, compressed carbon, and rubber. Other contemplated biomaterials include ceramics including, but not limited to, silicon nitride, silicon carbide, zirconia, and alumina, as well as glass, silica, and sapphire. Combinations of ceramics and metals can also be coated.

Metal and non-metal materials can be used to fabricate a variety of insertable articles. The medical article can be any that is introduced temporarily or permanently into a mammal for the prophylaxis or treatment of a medical condition. These articles include any that are introduced subcutaneously, percutaneously or surgically to rest within an organ, tissue, or lumen of an organ, such as arteries, veins, ventricles, or atria of the heart.

The inventive coating compositions can be utilized to coat virtually any medical article for which it is desired to provide a functional coating at a surface thereof. Exemplary medical articles include drug-delivering vascular stents (e.g., self-expanding stents typically made from nitinol, balloon-expanded stents typically prepared from stainless steel); other vascular devices (e.g., grafts, catheters, valves, artificial hearts, heart assist devices); implantable defibrillators; blood oxygenator devices (e.g., tubing, membranes); surgical devices (e.g., sutures, staples, anastomosis devices, vertebral disks, bone pins, suture anchors, hemostatic barriers, clamps, screws, plates, clips, vascular implants, tissue adhesives and sealants, tissue scaffolds); membranes; cell culture devices; chromatographic support materials; biosensors; shunts for hydrocephalus; wound management devices; endoscopic devices; infection control devices; orthopedic devices (e.g., for joint implants, fracture repairs); dental devices (e.g., dental implants, fracture repair devices), urological devices (e.g., penile, sphincter, urethral, bladder and renal devices, and catheters); colostomy bag attachment devices; ophthalmic devices; glaucoma drain shunts; synthetic prostheses (e.g., breast); intraocular lenses; respiratory, peripheral cardiovascular, spinal, neurological, dental, ear/nose/throat (e.g., ear drainage tubes); renal devices; and dialysis (e.g., tubing, membranes, grafts).

Other articles include urinary catheters (e.g., surface-coated with antimicrobial agents such as vancomycin or norfloxacin), intravenous catheters (e.g., treated with antithrombotic agents (e.g., heparin, hirudin, coumadin), small diameter grafts, vascular grafts, artificial lung catheters, atrial septal defect closures, electro-stimulation leads for cardiac rhythm management (e.g., pacer leads), glucose sensors (long-term and short-term), degradable coronary stents (e.g., degradable, non-degradable, peripheral), blood pressure and stent graft catheters, birth control devices, benign prostate and prostate cancer implants, bone repair/augmentation devices, breast implants, cartilage repair devices, dental implants, implanted drug infusion tubes, intravitreal drug delivery devices, nerve regeneration conduits, oncological implants, electrostimulation leads, pain management implants, spinal/orthopedic repair devices, wound dressings, embolic protection filters, abdominal aortic aneurysm grafts, heart valves (e.g., mechanical, polymeric, tissue, percutaneous, carbon, sewing cuff), valve annuloplasty devices, mitral valve repair devices, vascular intervention devices, left ventricle assist devices, neuro aneurysm treatment coils, neurological catheters, left atrial appendage filters, hemodialysis devices, catheter cuff, anastomotic closures, vascular access catheters, cardiac sensors, uterine bleeding patches, urological catheters/stents/implants, in vitro diagnostics, aneurysm exclusion devices, and neuropatches.

Other articles include, but are not limited to, vena cava filters, urinary dialators, endoscopic surgical tissue extractors, atherectomy catheters, clot extraction catheters, percutaneous transluminal angioplasty catheters (PTCA catheters), stylets (vascular and non-vascular), guidewires (such as coronary guidewires), drug infusion catheters, esophageal stents, circulatory support systems, angiographic catheters, transition sheaths and dialators, coronary and peripheral guidewires, hemodialysis catheters, neurovascular balloon catheters, tympanostomy vent tubes, cerebro-spinal fluid shunts, defibrillator leads, percutaneous closure devices, drainage tubes, thoracic cavity suction drainage catheters, electrophysiology catheters, stroke therapy catheters, abscess drainage catheters, biliary drainage products, dialysis catheters, central venous access catheters, and parental feeding catheters.

Other articles suitable for the present invention include, but are not limited to catheters (including vascular or urinary), guidewires, implantable vascular access ports, blood storage bags, vascular stents, blood tubing, vascular grafts, intraortic balloon pumps, cardiovascular sutures, total artificial hearts and ventricular assist pumps, extracorporeal devices such as blood oxygenators, blood filters, hemodialysis units, hemoperfusion units, plasmapheresis units, hybrid artificial organs such as pancreas or liver and artificial lungs, as well as filters adapted for deployment in a blood vessel in order to trap emboli (also known as "distal protection devices").

The coatings of the invention can be particularly useful for those articles that will come in contact with aqueous systems, such as bodily fluids.

One part of the coating process described herein provides the first coating composition to the surface of the article. In many aspects, when this composition is dried and the solvent sublimes from the coating material, a first coated layer is formed. The first coated layer can include polymeric component(s), for example, a diene polymer and optionally any other blended polymer, that are present in the coating composition and, optionally, other non-volatile components. Some or no residual levels of solvent may remain in the first coated layer. The first coated layer can become clad to the surface of the article, meaning that the polymeric material can become adhered to the surface with predominantly no covalent bonding between the polymeric material(s) (i.e., the diene polymers) of the first coated layer and the metal surface of the article.

In some modes of practice, the coating method is performed to provide a first coated layer having a thickness in the range of about 0.25 to 10 µm. The thickness of the coating can be affected by changing the concentration of the polymer in solution. That is, increasing the concentration of the polymer can provide a thicker first coated layer, while decreasing the concentration of the polymer can provide a thinner first coated layer.

The first coated layer is also compliant and conformal, meaning that it shapes well to the article to which is has been coated and that it can form to the changes in the shape of the article without introducing any substantial physical deformities.

After the first coated layer that contains the diene polymer has been formed on a surface of an article, one or more steps can be performed to form the second coated layer. In many aspects, a second coated layer can be formed by disposing a second coating composition that includes a hydrophilic polymer.

A second coated layer that includes a hydrophilic polymer can improve the lubricity of the surface and can facilitate movement of the article in the body. A lubricious coating formed on all or a portion of the medical article can reduce frictional forces, such as those that are present when the coated article is moved through a tissue or while in contact with a tissue. The coating can also reduce frictional forces when a coated medical article is used in combination with another medical article, for example, when a catheter is placed over a guidewire having the inventive coating as described herein.

In addition, the methods of the invention also been shown to provide a lubricious coating with increased durability. The increased durability can be seen when the coated article is subject to mechanical or physical challenge, such as manipulation of the coated article by bending, twisting, or turning, and/or when the article is in contact with a portion of the body or a portion of another medical article.

The hydrophilic polymer that is used to form the second coated layer can be a copolymer or a homopolymer. As used herein, the term "hydrophilic" refers to a polymer that is water-loving; typically, the hydrophilic polymers swell in the presence of water. In many aspects, a coating is formed wherein the hydrophilic polymer improves the lubricity of the article. As used herein, the term "lubricity" refers to a characterization of the frictional force associated with a coating. A coating with improved lubricity has a lower frictional force. Also, in many aspects, a coating is formed wherein the coating has improved durability. As used herein, the term "durability" refers to the wear resistance of a polymer coating, or the ability of a coating to adhere to an article surface when subjected to forces typically encountered during use (for example, normal force, shear force, and the like). A more durable coating is less easily removed from a substrate by abrasion. Durability of a coating can be assessed by subjecting the article to conditions that simulate use conditions. In preferred embodiments, the coating compositions preferably adhere to the article surface sufficiently to withstand the effect of shear forces encountered during insertion and/or removal of the article, which could otherwise result in delamination of the coating from the body member.

The hydrophilic polymer that is used to form the second coated layer can be a synthetic polymer, a natural polymer, or a derivative of a natural polymer.

In some embodiments the hydrophilic polymer is synthetic. Suitable synthetic hydrophilic polymers can be prepared from any suitable monomer including acrylic monomers, vinyl monomers, ether monomers, or combinations of any one or more of these. Acrylic monomers include, for example, methacrylate, methyl methacrylate, hydroxyethyl methacrylate, hydroxyethyl acrylate, methacrylic acid, acrylic acid, glycerol acrylate, glycerol methacrylate, acrylamide, methacrylamide, and derivatives and/or mixtures of any of these. Vinyl monomers include, for example, vinyl acetate, vinylpyrrolidone, vinyl alcohol, and derivatives of any of these. Ether monomers include, for example, ethylene oxide, propylene oxide, butylene oxide, and derivatives of any of these. Examples of polymers that can be formed from these monomers include poly(acrylamide), poly((meth)acrylamide, poly(vinylpyrrolidone), poly(acrylic acid), poly(ethylene glycol), poly(vinyl alcohol), and poly(HEMA). Examples of hydrophilic copolymers include, for example, methyl vinyl ether/maleic anhydride copolymers, vinyl pyrrolidone/methacrylamide copolymers, and vinyl pyrrolidone/acrylamide copolymers, and mixtures of any of these.

In some preferred embodiments, the hydrophilic polymer is a vinyl pyrrolidone polymer, acrylamide polymer, or vinyl pyrrolidone/(meth)acrylamide copolymer for example, poly(vinylpyrrolidone-co-(meth)acrylamide).

A mixture of hydrophilic polymers having different molecular weights can also be used to prepare the second coating layer. In one embodiment, a first hydrophilic polymer having an average molecular weight of at least about 500 kilodaltons (kD), or at least about 800 kD, is combined with a second hydrophilic polymer having an average molecular weight less than about 200 kD, or less than about 100 kD. For example, a first hydrophilic polymer having an average molecular weight in the range of about 500 to about 5000 kD, about 600 to about 2000 kD, or about 600 to about 1000 kD, can be combined with a second hydrophilic polymer having an average molecular weight in the range of about 10 to about 100 kD, about 15 to about 60 kD, or about 30 to about 60 kD. Not intending to be bound by a particular theory, it is theorized that the lower molecular weight material can migrate in the second coating layer and improve the lubricity of the second coating layer.

In some embodiments, only one molecular weight hydrophilic polymer is used in the second coating layer. For example, the second coating layer can be prepared using a hydrophilic polymer having an average molecular weight of at least about 500 kD or at least about 800 kD. The average molecular weight can be in the range of about 500 to about 5000 kD, about 600 to about 2000 kD, or about 600 to about 1000 kD. Not intending to be bound by a particular theory, it is thought that the absence of a lower molecular weight polymer such as a polymer having an average molecular weight less than about 200 kD, can, in some embodiments, improve the durability of the second coating layer.

In some embodiments the hydrophilic polymer is a natural polymer, or a derivative of a natural polymer. When desired, the inventive coating can include a hydrophilic polymer that provides biocompatibility to the surface of the article. If a biocompatible polymer is present in the coating, it is preferably present in the second coated layer. The biocompatible polymer can improve the function of the article in the body, by, for example, minimizing adverse reactions that can compromise the function of the article. In some aspects, the invention provides a biocompatible coating including a first coated layer comprising the diene polymer, and a second coated layer that contains a hydrophilic polymer that provides biocompatibility.

Examples of natural polymers include polysaccharides, such as glycosaminoglycans, and polypeptides, such as proteins. According to the invention, particularly useful polysaccharides can be selected from glycosaminoglycans such as heparin, heparan, hyaluronic acid, chondroitin, keratan, and dermatan. One example of a preferred polysaccharide is heparin; as used herein "heparin" refers to all forms of heparin, including sodium heparin, low molecular weight heparin, high affinity heparin, low affinity heparin, modified heparin, and treated heparin. Examples of other polysaccharides include those that are found in cell walls, such as alginic acid, alginate, chitosan, cellulose, and chitin. Other polysaccharides that can be used include dextrans, pectins, and starch. The second coated layer can also include mixtures of natural polymers, or mixtures of a natural hydrophilic polymer and a synthetic hydrophilic polymer.

Examples of natural hydrophilic polypeptides include polylysine, gelatin, collagen, laminin, and keratin. These polypeptides can be used to form the second coated layer to provide a surface to which tissues, cells, and components of body fluids, such as blood, can interact. Mixtures of natural hydrophilic polypeptides, and mixtures of natural hydrophilic polypeptides and synthetic hydrophilic polymers are also contemplated.

In other aspects of the invention a polymeric material is used to form the second coated layer that is different than a hydrophilic polymer. Examples of different polymeric materials include, for example, hydrophobic polymers and amphiphilic polymers.

In some aspects a latent reactive group is used to form the coating. The hydrophilic polymer of the second coated layer can be coupled with the first coating layer via a latent reactive group, such as a photoreactive group. In some embodiments, the latent reactive group can be provided as a separate component that is independent of the hydrophilic polymer, for example, as a photoreactive cross-linking agent. In other embodiments, the latent reactive group is part of the hydrophilic polymer, for example, as a reactive group pendent from the hydrophilic polymer. In yet other embodiments, the coating can be formed from latent reactive groups that are both pendent from and independent of the hydrophilic polymer. Generally, it is thought that in forming the coating, the latent reactive groups are activated when exposed to an appropriate activating source and react with the diene polymer, thereby coupling the hydrophilic polymer to the diene polymer.

In one preferred embodiment, the invention provides a medical article having a coating, wherein the medical article comprises a metal surface, and the coating comprises (a) a first coated layer that includes a diene polymer, wherein substantially no covalent bonds exist between the diene polymer and the metal surface, and (b) a second coated layer that includes a hydrophilic polymer, wherein the hydrophilic polymer is bonded to the first coated layer via latent reactive groups. Preferably, the hydrophilic polymer is bonded to the first coated layer via photoreactive groups. Preferably, the diene polymer of the first coated layer includes a butadiene polymer. The second coated layer can include polymers that give the surface distinct physical and chemical characteristics different than that of the first coated layer.

In another preferred embodiment, the invention provides a medical article having a coating, wherein the medical article comprises a metal surface that contains substantially no reactive metal species on its surface, and the coating comprises (a) a first coated layer that includes a diene polymer, and (b) a second coated layer that includes a hydrophilic polymer, and wherein latent reactive groups have been activated and reacted to bond the hydrophilic polymer to the diene polymer.

The latent reactive groups can allow the hydrophilic polymer to be bonded to the first coated layer in a number of ways. In some aspects, the latent reactive groups are provided in the second coating composition and then activated to bond the hydrophilic polymer to the first coated layer. In other aspects, the latent reactive groups are disposed between the first coated layer that includes the diene polymer, for example, poly(butadiene), and the second coated layer that includes the hydrophilic polymer. Optionally, the latent reactive groups can be present in between the first coated layer and the second coated layer, and within the second coated layer.

In a preferred aspect, the invention provides a method for forming a coating for a medical article comprising a metal surface, the coating including the steps of (a) disposing a composition comprising a diene polymer, such as a butadiene polymer, on the metal surface to form a first coated layer, and (b) disposing a composition comprising a hydrophilic polymer and latent reactive groups on the first coated layer, and (c) treating the latent reactive groups to couple the hydrophilic polymer to the first coated layer. In another preferred aspect of the invention, the metal surface is not pre-derivatized to provide a reactive metal species on the surface of the article.

Latent reactive groups, broadly defined, are groups that respond to specific applied external stimuli to undergo active specie generation with resultant covalent bonding to a target, such as thermal or actinic energy. Latent reactive groups are those groups of atoms in a molecule that retain their covalent bonds unchanged under conditions of storage but which, upon activation, form covalent bonds with other molecules. The latent reactive groups generate active species such as free radicals, nitrenes, carbenes, and excited states of ketones upon absorption of external electromagnetic or kinetic (thermal) energy. Latent reactive groups may be chosen to be responsive to various portions of the electromagnetic spectrum, and latent reactive groups that are responsive to ultraviolet, visible or infrared portions of the spectrum are preferred. Latent reactive groups, including those that are described herein, are well known in the art. The present invention contemplates the use of any suitable latent reactive group for formation of the inventive coatings as described herein.

Latent reactive groups include photoreactive groups that respond to specific applied external stimuli to undergo active specie generation with resultant covalent bonding to an adjacent chemical structure, for example, as provided by the same or a different molecule. Latent reactive groups, including photoreactive groups, are those groups of atoms in a molecule that retain their covalent bonds unchanged under conditions of storage but that, upon activation by an external energy source, can form covalent bonds with other molecules. See, for example, U.S. Pat. No. 5,002,582 (Guire et al., "Preparation of Polymeric Surfaces Via Covalently Attaching Polymers").

Photoreactive groups can generate active species such as free radicals and particularly nitrenes, carbenes, and excited states of ketones, upon absorption of electromagnetic energy. Photoreactive groups can be chosen to be responsive to various portions of the electromagnetic spectrum, and that are responsive to the ultraviolet and visible portions of the spectrum are preferred.

Photoreactive aryl ketones are preferred, such as acetophenone, benzophenone, quinone, anthraquinone, anthrone, and anthrone-like heterocycles (for example, heterocyclic analogs of anthrone such as those having nitrogen, oxygen, or sulfur in the 10-position), or their substituted (for example, ring substituted) derivatives. Examples of preferred aryl ketones include heterocyclic derivatives of anthrone, including acridone, xanthone, and thioxanthone, and their ring substituted derivatives. Some preferred photoreactive groups are thioxanthone, and its derivatives, having excitation energies greater than about 360 nm.

The functional groups of such ketones are preferred since they are readily capable of undergoing the activation/inactivation/reactivation cycle described herein. Benzophenone is a particularly preferred latent reactive moiety, since it is capable of photochemical excitation with the initial formation of an excited singlet state that undergoes intersystem crossing to the triplet state. The excited triplet state can insert into carbon-hydrogen bonds by abstraction of a hydrogen atom (from a support surface, for example), thus creating a radical pair. Subsequent collapse of the radical pair leads to formation of a new carbon-carbon bond. If a reactive bond (for example, carbon-hydrogen) is not available for bonding, the ultraviolet light-induced excitation of the benzophenone group is reversible and the molecule returns to ground state energy level upon removal of the energy source. Photoactivatable aryl ketones such as benzophenone and acetophenone are of particular importance inasmuch as these groups are subject to multiple reactivation in water and hence provide increased coating efficiency.

The azides constitute another class of photoreactive groups and include arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benezensulfonyl azide; and phosphoryl azides [$(RO)_2PON_3$] such as diphenyl phosphoryl azide and diethyl phosphoryl azide.

Diazo compounds constitute another class of photoreactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetatoacetates (—CO—$CN_2CO$—O—) such as t-butyl alpha diazoacetoacetate.

Other photoreactive groups include the diazirines (—$CHN_2$) such as 3-trifluoromethyl-3-phenyldiazirine; and ketenes (CH=C=O) such as ketene and diphenylketene.

Peroxy compounds are contemplated as another class of latent reactive groups which can be thermally activated and include dialkyl peroxides such as di-t-butyl peroxide and dicyclohexyl peroxide and diacyl peroxides such as dibenzoyl peroxide and diacetyl peroxide and peroxyesters such as ethyl peroxybenzoate.

In some aspects, the photoreactive group can be provided as part of the hydrophilic polymer of the second coating composition or second coated layer. In these aspects, the second coated layer can include a photopolymer. As used herein, the term "photopolymer" refers to a polymer having one or more attached photoreactive groups. The photoreactive group is typically pendent from the polymeric portion of the hydrophilic polymer. The photoreactive group can be any of those discussed herein as suitable latent photoreactive groups, including those that can be used in the photoactivatable cross-linking agent. In some embodiments, the latent photoreactive group is an aryl ketone or a quinone.

The polymeric portion of the photopolymer can be either a homopolymer or a copolymer, and typically is hydrophilic and/or biocompatible. Any of the hydrophilic polymers described herein can provide the polymeric portion of the photopolymer.

The photopolymer can be formed using any sort of synthetic process that will result in the formation of a hydrophilic polymer with one or more pendent photoreactive groups. The photoreactive groups can be present at the terminal portions (ends) of the polymeric strand or can be present along the length of the polymer, or combinations thereof. In one embodiment the photoreactive groups are located randomly along the length of the polymer.

The photopolymer can be synthesized by attaching photoreactive groups to a "preformed" hydrophilic polymer. The preformed polymer can be obtained from a commercial source or be synthesized from the polymerization of a desired monomer or combination of different monomers. In one example of preparing the photopolymer, a moiety that includes a photoreactive group and a first reactive group is reacted with a portion of a hydrophilic polymer that is reactive with the first reactive group, resulting in the formation of a hydrophilic polymer having a pendent photoreactive group. The reaction preferably does not result in the activation of the photoreactive group; therefore the photoreactive group remains "latent" and capable of activation by actinic radiation during the coating process. Such attachments of the photoreactive group can be achieved by, for example, substitution or addition reactions.

For example, in one embodiment, the polymeric portion of the photopolymer is formed by reacting acrylamide, 2-acrylamide-2-methylpropane sulfonic acid, and N-(3-aminopropyl) methacrylamide. In another embodiment, the polymeric portion is prepared by the copolymerization of 1-vinyl-2-pyrrolidone and N-(3-aminopropyl) methacrylamide. The copolymers are derivatized with an acyl chloride (such as, for example, 4-benzoylbenzoyl chloride) under Schotten-Baumann conditions to form photo-poly(vinylpyrrolidone) (also referred to as "photo-PVP"). That is, the acyl chloride reacts with the amino group of the N-(3-aminopropyl) moiety of the copolymer. An amide is formed resulting in the attachment of the aryl ketone to the polymer. The liberated hydrochloric acid is neutralized with an aqueous base solution.

Photoderivatized polysaccharides, such as heparin ("photo-heparin") can be prepared by those skilled in the art as well, for example, in the manner described in U.S. Pat. No. 5,563,056 (Swan et al., see Example 4), which describes the preparation of photo-heparin by reacting heparin with benzoyl-benzoyl-epsilon-aminocaproyl-N-oxysuccinimide in dimethylsulfoxide/carbonate buffer. The solvent was evaporated and the photo-heparin was dialyzed against water, lyophilized, and then dissolved in water.

In another method of preparing the photopolymer, monomers having photoreactive groups are obtained or prepared. These monomers are then co-polymerized with other monomers that do not have photoreactive groups to create a photopolymer. This is a particularly suitable way for preparing photopolymers that have desired amount of photoreactive groups, and desired monomeric units. A useful polymerizable mixture of monomers for preparation of the photopolymer includes, for example, from about 0.1% to about 10% of a photoreactive group-monomer, and from about 90% to about 99.9% of a hydrophilic monomer, or combination of hydrophilic monomers, as based on a molar percentage of the total amount of monomers present in the mixture. The photo monomers used to prepare the photopolymer can include any suitable polymerizable portion, such as, for example, acrylic monomers, vinyl monomers, or ether monomers.

Photo-polyacrylamide can be prepared by copolymerizing a methacrylamide having a photoreactive group with acrylamide. The photo acrylamide can be prepared according to the process described in U.S. Pat. No. 6,007,833 (see Examples 1 & 2). A methacrylamide-oxothioxanthene monomer (N-[3-(7-methyl-9-oxothioxanthene-3-carboxamido) propyl]methacrylamide (MTA-APMA)) can be prepared by reacting 7-methyl-9-oxothioxanthene-3-carboxylic acid chloride (MTA-Cl) with N-(3-aminopropyl)methacrylamide hydrochloride (APMA). MTA-APMA can then be copolymerized with acrylamide in DMSO in the presence of a chain transfer agent, a co-catalyst, and a free radical initiator. MTA-APMA can then be copolymerized with other types of monomers, such as vinyl pyrrolidone, to produce other photo-polymers (see also U.S. Pat. No. 6,007,833).

The coating can also be prepared using at least one photoactivatable cross-linking agent that can be non-ionic or ionic. The photoactivatable cross-linking agent has at least two latent photoreactive groups that can become chemically reactive when exposed to an appropriate actinic energy source. The coating can be formed by including a photoactivatable cross-linking agent in the second coating composition along with the hydrophilic polymer. Alternatively, the photoactivatable cross-linking agent can be used independently of the second coating composition.

For example, the photoactivatable cross-linking agent can be disposed after disposing the first coating composition but before the second coating composition. In this aspect, a method for forming the coating can include the steps of: (a) disposing a composition comprising a diene polymer, such as a butadiene polymer, to form a first coated layer (b) disposing a crosslinking agent comprising pendent latent reactive groups, such as photoreactive groups, (c) disposing a composition comprising a hydrophilic polymer, and (d) treating the latent reactive groups to couple the hydrophilic polymer to the first coated layer.

In some embodiments of the invention, it is thought that the non-ionic photoactivatable cross-linking agent migrates towards the interface between the materials present in the first layer and the second layer. The tendency to migrate may be attributable to the hydrophobic nature and the relatively low molecular weight of the non-ionic photoactivatable cross-linking agent. In such embodiments, the non-ionic photoactivatable cross-linking agent facilitates the attachment of the polymer of the second layer to the material of the first layer. For example, upon activation, a covalent bond can be formed between the non-ionic photoactivatable cross-linking agent and at least one of the compounds in the first coating layer and at least one of the compounds in the second coating layer.

Any suitable non-ionic photoactivatable cross-linking agent can be used. In one embodiment, the non-ionic photoactivatable cross-linking agent has the formula $XR_1R_2R_3R_4$, where X is a chemical backbone, and $R_1$, $R_2$, $R_3$, and $R_4$ are radicals that include a latent photoreactive group. Exemplary non-ionic cross-linking agents are described, for example, in U.S. Pat. Nos. 5,414,075 and 5,637,460 (Swan et al., "Restrained Multifunctional Reagent for Surface Modification"). These patents describe coating reagents that include a chemical backbone having attached to it one or more first photoreactive groups capable of attaching to a surface, and one or more second photoreactive groups capable of attaching to a target molecule of interest. Optionally, the coating reagents further include spacers that couple the latent reactive groups with the chemical backbone. Chemically, the first and second photoreactive groups, and respective spacers, can be the same or different.

Preferably, the photoreactive groups of the non-ionic cross-linking agent are adapted to undergo reversible photolytic homolysis, thereby permitting photoreactive groups that are not consumed in attachment to the first coating layer to revert to an inactive, or "latent" state. These photoreactive groups can be subsequently activated, in order to attach to any compound in the second coating layer with an abstractable hydrogen for covalent bond formation. Thus, excitation of the photoreactive group is reversible and the group can return to a ground state energy level upon removal of the energy source. In some embodiments, preferred non-ionic cross-linking agents are those groups that can be subject to multiple activations and hence provide increased coating efficiency.

In situations in which all photoreactive groups and spacers are chemically, or at least functionally, the same, the distinction between first and second photoreactive groups can actually be accomplished at the time of the first activation step; that is, those groups that are activated and attach to the surface will be considered "first" photoreactive groups, and those that remain unreacted (whether or not they have been activated) will be considered "second" photoreactive groups.

In some embodiments, the first and second photoreactive groups are coupled to the chemical backbone by spacer chains in such a manner that, upon activation of the photoreactive groups in the presence of a support surface, the first photoreactive groups are capable of covalently bonding to a component of the first coated layer. The second photoreactive groups are thereby conformationally restricted, thus preventing reaction with their spacers, other restricted reagents of the same type, and/or the first coating layer. In addition, after the first activation step and removal of the activating stimulus (for example, an illumination source), the second photoreactive groups are capable of reverting to their inactivate state and can thereafter be activated (or reactivated, as the case may be) to that excited compound in triplet state.

Some suitable cross-linking agents are those formed by a mixture of the chemical backbone molecule (such as pentaerythritol) and an excess of a derivative of the photoreactive group (such as 4-bromomethylbenzophenone). An exemplary product is tetrakis (4-benzoylbenzyl ether) of pentaerythritol (tetrakis(4-benzoylphenylmethoxymethyl)methane). See U.S. Pat. Nos. 5,414,075 and 5,637,460.

In some aspects, the photoactivatable cross-linking agent can be ionic. Thus, in some embodiments, at least one ionic photoactivatable cross-linking agent is used to form the coating. In some cases, an ionic photoactivatable cross-linking agent can be used to crosslink the polymers within the second coating layer which can also improve the durability of the coating.

Any suitable ionic photoactivatable cross-linking agent can be used. In some embodiments, the ionic photoactivatable cross-linking agent is a compound of formula I:

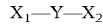

where Y is a radical containing at least one acidic group, basic group, or a salt of an acidic group or basic group. $X_1$ and $X_2$ are each independently a radical containing a latent photoreactive group.

The photoreactive groups can be the same as those described herein. Spacers can also be part of $X_1$ or $X_2$ along with the latent photoreactive group. In some embodiments, the latent photoreactive group includes an aryl ketone or a quinone.

The radical Y in formula I provides the desired water solubility for the ionic photoactivatable cross-linking agent. The water solubility (at room temperature and optimal pH) is at least about 0.05 mg/ml. In some embodiments, the solubility is about 0.1 to about 10 mg/ml or about 1 to about 5 mg/ml.

In some embodiments of formula I, Y is a radical containing at least one acidic group or salt thereof. Such a photoactivatable cross-linking agent can be anionic depending upon the pH of the coating composition. Suitable acidic groups include, for example, sulfonic acids, carboxylic acids, phosphonic acids, and the like. Suitable salts of such groups include, for example, sulfonate, carboxylate, and phosphate salts. In some embodiments, the ionic cross-linking agent includes a sulfonic acid or sulfonate group. Suitable counter ions include alkali, alkaline earths metals, ammonium, protonated amines, and the like.

For example, a compound of formula I can have a radical Y that contains a sulfonic acid or sulfonate group; $X_1$ and $X_2$ can contain photoreactive groups such as aryl ketones. Such compounds include 4,5-bis(4-benzoylphenylmethyleneoxy) benzene-1,3-disulfonic acid or salt; 2,5-bis(4-benzoylphenylmethyleneoxy)benzene-1,4 -disulfonic acid or salt; 2,5-bis(4-benzoylmethyleneoxy)benzene-1-sulfonic acid or salt; N,N-bis[2-(4-benzoylbenzyloxy)ethyl]-2-aminoethanesulfonic acid or salt, and the like. See U.S. Pat. No. 6,278,018. The counter ion of the salt can be, for example, ammonium or an alkali metal such as sodium, potassium, or lithium.

In other embodiments of formula I, Y can be a radical that contains a basic group or a salt thereof. Such Y radicals can include, for example, an ammonium, a phosphonium, or a sulfonium group. The group can be neutral or positively charged, depending upon the pH of the coating composition. In some embodiments, the radical Y includes an ammonium group. Suitable counter ions include, for example, carboxylates, halides, sulfate, and phosphate.

For example, compounds of formula I can have a Y radical that contains an ammonium group; $X_1$ and $X_2$ can contain photoreactive groups that include aryl ketones. Such photoactivatable cross-linking agents include ethylenebis(4-benzoylbenzyldimethylammonium) salt; hexamethylenebis (4-benzoylbenzyldimethylammonium) salt; 1,4-bis(4-benzoylbenzyl)-1,4-dimethylpiperazinediium) salt, bis(4-benzoylbenzyl)hexamethylenetetraminediium salt, bis[2-(4-benzoylbenzyldimethylammonio)ethyl]-4-benzoylbenzylmethylammonium salt; 4,4-bis(4-benzoylbenzyl)morpholinium salt; ethylenebis[(2-(4-benzoylbenzyldimethylammonio)ethyl)-4-benzoylbenzylmethylammonium] salt; and 1,1,4,4-tetrakis (4-benzoylbenzyl)piperazinediium salt. See U.S. Pat. No. 5,714,360. The counter ion is typically a carboxylate ion or a halide. On one embodiment, the halide is bromide.

A single photoactivatable cross-linking agent or any combination of photoactivatable cross-linking agents can be used in forming the coating. In some embodiments, at least one nonionic cross-linking agent such as tetrakis (4-benzoylbenzyl ether) of pentaerythritol can be used with at least one ionic cross-linking agent. For example, at least one non-ionic photoactivatable cross-linking agent can be used with at least one cationic photoactivatable cross-linking agent such as an ethylenebis(4-benzoylbenzyldimethylammonium) salt or at least one anionic photoactivatable cross-linking agent such as 4,5-bis (4-benzoylphenylmethyleneoxy)benzene-1,3-disulfonic acid or salt. In another example, at least one nonionic cross-linking agent can be used with at least one cationic cross-linking agent and at least one anionic cross-linking agent. In yet another example, a least one cationic crosslinking agent can be used with at least one anionic crosslinking agent but without the addition of a non-ionic crosslinking agent.

The second coating can be formed in a manner that allows the hydrophilic polymer of the second coating composition to be coupled to materials of the first coated layer. The coupling is performed via reactive latent groups, which can ultimately serve to bond the hydrophilic polymer to, for example, the diene polymer of the first coated layer.

The process of forming the second coated layer can be performed by disposing the hydrophilic polymer in a composition with the latent reactive group, or by disposing the hydrophilic polymer in a composition independent of the latent reactive group. From the standpoint of efficiency, a process wherein the hydrophilic polymer is disposed with the latent reactive group may be preferred. It is understood that in these approaches the first coated layer that includes the diene polymer has already been formed.

The process of forming the second coated layer can involve preparing a second coating composition that includes a hydrophilic polymer and a latent reactive group, such as a photoreactive group. In this approach the hydrophilic polymer can be pendent or independent of the latent reactive group.

In the second coating composition, the hydrophilic polymer (with or without pendent latent reactive groups) can be dissolved or suspended in an aqueous solvent at a concentration that allows the formation of a second coated layer that has one or more desired properties, such as lubricity, durability, biocompatibility, and/or other physical properties such as thickness. In some aspects, the concentration of the hydrophilic polymer, such as a photopolymer, in the second coating composition is in the range from about 10 mg/ml to about 50 mg/ml.

In some aspects, the second coating composition includes a hydrophilic polymer and latent reactive groups that are not pendent from the hydrophilic polymer, such as latent reactive groups that are included in a crosslinking agent. These compositions can include photocrosslinking agents in compositions that include photopolymers, non-photopolymers, or combinations of both photopolymers and non-photopolymers. In some aspects, useful concentrations of the photocrosslinking agent in the second coating composition are in the range from about 0.15 mg/ml to about 1.0 mg/ml.

In one embodiment, the second coated layer is formed by a process that includes disposing the latent reactive groups, such as photoreactive groups, on the first coated layer prior to disposing the hydrophilic polymer. For example, a composition that includes a photocrosslinking agent can be prepared and then disposed on the first coated layer. If desired, a step of treating the photocrosslinking agent can be performed prior to disposing the second coating composition containing the hydrophilic polymer. If this step is performed it can be done in such a manner as to promote the activation and bonding of at least one of the at least two photoreactive groups of the crosslinking agent to the first coated layer. Preferably, one or more other photoreactive groups of the bonded crosslinking agent remain latent or revert to a latent state, and remain capable of being activated and bonding to the hydrophilic polymer in a subsequent step.

Alternatively, the photoreactive crosslinking agent can be disposed on the first coated layer, followed by disposing the second coating composition, and then the surface can be irradiated to activate the photoreactive group and bond the hydrophilic polymer to the first coated layer.

In embodiments a step of irradiating can be performed by subjecting the photoreactive groups to actinic radiation in an amount that promotes formation of the second coated layer. During irradiation, the photoreactive groups are typically disposed on the first coated layer; therefore, the article is subject to an activating dose of irradiation.

Actinic radiation can be provided by any suitable light source that promotes activation of the photoreactive groups. Preferred light sources (such as those available from Dymax Corp.) provide UV irradiation in the range of 190 nm to 360 nm. A suitable dose of radiation is in the range of from about 0.5 mW/cm$^2$ to about 2.0 mW/cm$^2$.

In some aspects, it may be desirable to use filters in connection with the step of activating the photoreactive groups. The use of filters can be beneficial from the standpoint that they can selectively minimize the amount of radiation of a particular wavelength or wavelengths that are provided to the coating during the activation process. This can be beneficial if one or more components, such as a bioactive agent, of the coating are sensitive to radiation of a particular wavelength(s), and that may degrade or decompose upon exposure.

Typically, filters are identified by the wavelength of light that is permitted to pass through the filter. Two illustrative types of filters that can be used in connection with the invention are cut-off filters and band pass filters. Generally, cut-off filters are categorized by a cut-off transmittance, at which the light transmittance is approximately 25% of the maximum transmittance. For band pass filters, a range of wavelength is identified for the filter, and the center wavelength is the midpoint of wavelength allowed through; at midpoint, the transmittance is approximately half of the maximum transmittance allowed through the filter.

Thus, in one embodiment utilizing a band pass filter, for example, an Edmund 407 nm filter, the filter can be chosen that has a maximum UV transmittance at its center wavelength of 407 nm. In another embodiment, a band pass filter having a maximum transmittance at 500 nm is used.

Another aspect of the invention relates to coatings for medical article that comprise a cylindrical shape with an exterior surface, an interior surface, a first end, a second end, and a plurality of openings between the first and second ends. The coating method includes the steps of (a) disposing a composition comprising a first polymer to form a first coated layer on the exterior and interior surfaces of the article, wherein the first coated layer substantially bridges the openings in the article, and (b) disposing a composition comprising a second polymer to form a second coated layer on the exterior surface of the article.

The method can be used to form coating on the exterior of the article that is lubricious. An exemplary article is a wire formed into a helical shape, for example, a coil. In this article gaps between the coiled wire represent the openings between the first and second ends. The method can be used to provide such a coating to medical articles selected from the group consisting of guidewires and catheter coils.

In order to demonstrate these aspects of the invention, which involves forming a first and second coated layer on the surface of the article, reference is made to FIG. 1. FIG. 1 relates to embodiments wherein the first coated layer is used to promote formation of the second coated layer on only a portion of the surface of the article. In this embodiment, an article having an inner and outer surface, and having openings from the outer to the inner surface, is coated with a first coating composition and then coated with a second coating composition. The second coating composition is only coated on the outer surface because the first coated layer hinders the second coating composition from being disposed on the inner surface. In this embodiment, and referring to FIG. 1(a), an exemplary article is a helically wound wire 10 (i.e., a coil). Referring to FIG. 1(b), which is a cross sectional view of the helically wound coil 10, the coil wire structure 12 has an outer surface 14 and an inner surface 16 and has gaps 18 between the coiled wire structure 12 which represent the openings between the first and second ends. In some aspects, the plurality of openings comprises an opening having a width of 76 µm or less.

Referring to FIG. 1(c), a first coating composition comprising a diene polymer is disposed to form a first coated layer 20 on the entirety of the coil surface (including inner surface 16 and outer surfaces 14). In forming the first coated layer 20, the openings (gaps 18) in the article are blocked to the extent that they prevent a subsequently applied coating material from entering the openings. Subsequently, and referring to FIG. 1(d), a second coating composition is disposed on the outer surface 14 of the article, wherein the second composition is prevented from being contacting the inner surface 16, and forms a second coated layer 22 on the outer surface 14 of the article. The second coating composition can include material that is coupled to the first coated layer, and can include a hydrophilic polymer and photoreactive groups.

This allows the formation of a lubricious coating on an outer surface of an article, where in use, the outer surface is in contact with a tissue and the lubricious coating facilitates movement of the surface over the tissue. On the inside of the article the surface preferably has a different property than the outer surface, such as lower levels of lubricity, as the inner surface can be in contact with another portion of the article where frictional forces are desired.

The invention will be further described with reference to the following non-limiting Examples.

Friction Testing

Friction testing of the substrates was performed in the following manner. The substrate was hydrated in isotonic saline and was pulled between two silicone pads exerting 200 g force on the wire. The pull force exerted on the substrate was then measured (grams). Pull force (g) is equal to the coefficient of friction (COF) multiplied by pinch force (g). The pull force was averaged over a 20 cm second and the pulls were repeated 15 times.

EXAMPLE 1

The present example describes a coating process wherein substrates were provided with a poly(diene) base coat followed by a second coat with a photo-poly(vinylpyrrolidone) coating solution. The coated substrates were tested for lubricity after coating formation.

Stainless steel guidewires (0.254 mm O.D.; Small Parts, Inc, FL) and white PEBAX rods (3 mm O.D.; Medsource, Inc., MN) were dip-coated in a poly(1,2 butadiene) solution. In order to prepare the poly(1,2 butadiene) coating solution, 5 g of pelleted poly(1,2 butadiene) (Scientific Polymer Products; Ontario, N.Y.) was dissolved to a concentration of 50 mg/ml in tetrahydrofuran (THF). The PEBAX rods or stainless steel guide wire were immersed in the poly(1,2 butadiene) coating solution at a temperature of 22° C. for a period of 20 seconds. The substrates were then removed and air-dried for 15 minutes.

For the second coat, a solution of photo-poly(vinylpyrrolidone) was prepared. Photo-poly(vinylpyrrolidone) was made by the copolymerization of 1-vinyl-2-pyrrolidone (Aldrich) and N-(3-aminopropyl) methacrylamide, as described in Example 2 of U.S. Pat. No. 5,858,653. Photoderivatization of the polymer using 4-benzoylbenzoyl chloride was prepared as described in Example 2 of U.S. Pat. No. 5,858,653, under Schotten-Baumann conditions (a two phase aqueous/organic reaction system).

To apply the second coating layer, the polybutadiene coated stainless steel guidewires or PEBAX rods were dip-coated into the photo-poly(vinylpyrrolidone) coating solution at a rate of 1 cm /sec., dwelling for 30 seconds, and withdrawing at a rate of 0.5 cm/sec. After removal of the coated substrates from the photo-poly(vinylpyrrolidone) coating solution, the substrates were air-dried for 10 minutes.

After the second coat was applied to the substrates, the substrates were illuminated with a Dymax lamp (model no. PC-2, Dymax Corporation, Torrington, Conn.) having a Heraeus bulb (W. C. Heraeus GmbH, Hanau, Federal Republic of Germany). The coated substrates were suspended midway between the opposed Dymax lamps, approximately 40 cm apart. The illumination duration was for 3 minutes at an intensity of 1-2 mW/cm$^2$ in the wavelength range of 330-340 nm. After irradiation the coated substrates were immersed in deionized water for ten seconds to hydrate the surface and then tested for frictional force using the Friction Testing assay as described herein.

After coating, the PEBAX rods or stainless steel guidewires were evaluated for lubricity/durability by friction measurements using a Vertical Pinch Method as described in International Application Number WO 03/055611 with the following modifications. The coated PEBAX rods or Stainless Steel guidewires were inserted into the end of a rod holder, which was placed between the two jaws of a pinch tester and immersed in a cylinder of water or saline. The jaws of the pinch tester were closed as the sample was pulled in a vertical direction and opened when the coated sample was returned to the original position. A 500 g force (load) was applied as the sample rod or guidewire was pulled up through the pinched jaws. The average frictional force was determined for 5 cycles while the coated rod or guidewire traveled 3 cm at a travel rate of 0.5 mm/sec. While uncoated PEBAX rods exhibited friction forces of 400 grams, the coated PEBAX rods exhibited friction forces of approximately 10 grams. Uncoated stainless steel wires exhibited friction forces of approximately 300 grams, and the coated stainless steel wires exhibited friction forces of approximately 5 grams. The results show that the coating remained lubricious and durable over 5 cycles.

What is claimed is:

1. An insertable medical article having a structure with a coating thereon, the coating comprising
   a first coated layer comprising a diene homopolymer; and
   a second coated layer comprising a hydrophilic polymer, the first coated layer being closer to the structure than the second coated layer,
   wherein there are substantially no covalent bonds between the diene homopolymer and the structure.

2. The medical article of claim 1 wherein the second coated layer is in contact with the first coated layer.

3. The medical article of claim 2 wherein the hydrophilic polymer is covalently bonded to the diene homopolymer.

4. The medical article of claim 3 wherein the hydrophilic polymer is covalently bonded to the diene homopolymer via a latent reactive group.

5. The medical article of claim 1 wherein the diene homopolymer is a poly(butadiene) homopolymer.

6. The medical article of claim 5 wherein the diene homopolymer is poly(1,2 butadiene).

7. The medical article of claim 1 wherein the diene homopolymer has a Tg in the range of −40° C. to 0° C.

8. The medical article of claim 7 wherein the diene homopolymer has a Tg in the range of −15° C. to 0° C.

9. The medical article of claim 1 wherein the structure comprises a metal surface.

10. The medical article of claim 1 comprising an insertable medical article selected from the group consisting of wires, balloons, distal protection devices, stents, and coils.

11. The medical article of claim 1 wherein the first coated layer comprises a bioactive agent.

12. The medical article of claim 1 having a cylindrical shape defined by the structure having an exterior surface, an interior surface, a first end, a second end, and a plurality of openings through the structure between the first and second ends, wherein the first coated layer is formed on both the exterior surface and the interior surface of the structure, and wherein the first coated layer substantially bridges the openings in the structure, and wherein the second coated layer is formed on the first coated layer on the exterior surface.

13. The medical article of claim 12, wherein each of the plurality of openings comprises an opening having a width of 76 μm or less.

14. The medical article of claim 12 comprising a coil.

15. An insertable medical article having a cylindrical shape defined by a structure having an exterior surface, an interior surface, a first end, a second end, and a plurality of openings through the structure between the first and second ends, a first coated layer comprising a polymeric material formed on both the exterior surface and the interior surface of the structure, wherein the first coated layer substantially bridges the plurality of openings, and a second coated layer comprising a second polymer formed on the first coated layer on the exterior surface.

16. The medical article of claim 1 wherein the diene homopolymer is made from a monomer selected from the group consisting of:

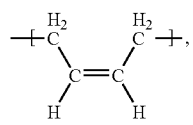
(a)

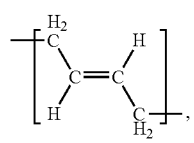
(b)

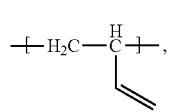
(c)

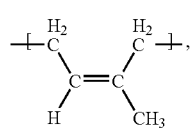
(d)

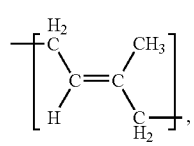
(e)

-continued

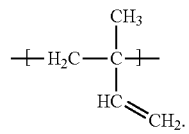
(f)

17. The medical article of claim 1 wherein the second coated layer comprises photoreactive groups that have been treated to bond the hydrophilic polymer to the first coated layer.

18. The medical article of claim 17 wherein the photoreactive groups that have been treated to bond the hydrophilic polymer to the first coated layer are pendent from the hydrophilic polymer.

19. The medical article of claim 17 wherein the photoreactive groups that have been treated to bond the hydrophilic polymer to the first coated layer are present on a non-ionic cross-linking agent comprising at least two photoreactive groups.

20. An insertable medical article having a structure with a coating thereon, the coating comprising a first coated layer comprising a diene polymer having a Tg in the range of −40° C. to 0° C.; and a second coated layer comprising a hydrophilic polymer, the first coated layer being closer to the structure than the second coated layer, wherein there are substantially no covalent bonds between the diene polymer and the structure.

21. The medical article of claim 20 wherein the diene polymer comprises a monomer selected from the group consisting of:

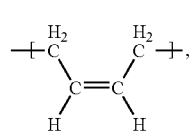
(a)

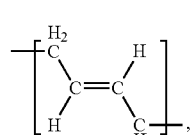
(b)

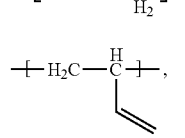
(c)

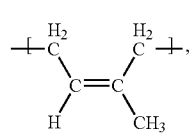
(d)

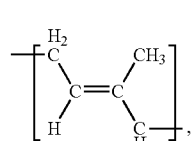
(e)

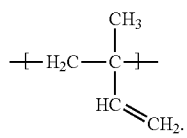
(f)

22. The medical article of claim 21 wherein the diene polymer comprises 1,2 butadiene.

23. The medical article of claim 20 where, in the diene polymer, greater than 50% of the monomeric units are butadiene monomeric units.

24. The medical article of claim 20 wherein the hydrophilic polymer is covalently bonded to the diene polymer, and the second coated layer comprises photoreactive groups that have been treated to bond the hydrophilic polymer to the first coated layer.

* * * * *